(12) United States Patent
Zhao et al.

(10) Patent No.: US 9,902,680 B2
(45) Date of Patent: Feb. 27, 2018

(54) METHOD FOR PROCESSING ACETIC ACID SOLVENT IN OXIDISING UNIT OF PTA INDUSTRIAL APPARATUS

(71) Applicant: TIANHUA INSTITUTE OF CHEMICAL MACHINERY AND AUTOMATION CO., LTD, Gansu (CN)

(72) Inventors: Xu Zhao, Gansu (CN); Wanyao Zhang, Gansu (CN); Zhongxin Sun, Gansu (CN); Maikui Zhang, Gansu (CN); Yongpeng Tan, Gansu (CN); Xiangnan Zhai, Gansu (CN); Tianbao Wang, Gansu (CN); Tao Shen, Gansu (CN); Rui Wang, Gansu (CN); Yuanyue Liang, Gansu (CN); Xiaopeng Feng, Gansu (CN); Guohai Zhang, Gansu (CN)

(73) Assignee: TIANHUA INSTITUTE OF CHEMICAL MACHINERY AND AUTOMATION CO., LTD, Gansu (CN)

( * ) Notice: Subject to any disclaimer, the term of this patent is extended or adjusted under 35 U.S.C. 154(b) by 0 days.

(21) Appl. No.: 15/312,504

(22) PCT Filed: Feb. 11, 2015

(86) PCT No.: PCT/CN2015/072719
§ 371 (c)(1),
(2) Date: Nov. 18, 2016

(87) PCT Pub. No.: WO2015/176562
PCT Pub. Date: Nov. 26, 2015

(65) Prior Publication Data
US 2017/0081269 A1 Mar. 23, 2017

(30) Foreign Application Priority Data

May 20, 2014 (CN) .......................... 2014 1 0211789

(51) Int. Cl.
| | | |
|---|---|---|
| C07C 51/42 | (2006.01) | |
| C07C 51/47 | (2006.01) | |
| B01D 25/12 | (2006.01) | |
| C07C 53/08 | (2006.01) | |
| C07C 63/26 | (2006.01) | |

(52) U.S. Cl.
CPC .............. *C07C 51/47* (2013.01); *B01D 25/12* (2013.01); *C07C 53/08* (2013.01); *C07C 63/26* (2013.01)

(58) Field of Classification Search
CPC ......... C07C 51/47; C07C 53/08; C07C 63/26; B01D 25/12
See application file for complete search history.

(56) References Cited

FOREIGN PATENT DOCUMENTS

| | | |
|---|---|---|
| CN | 1150945 A | 6/1997 |
| CN | 101045683 A | 10/2007 |
| CN | 201534023 A | 7/2010 |
| CN | 102381964 A | 3/2012 |
| CN | 102476994 A | 5/2012 |
| CN | 202270412 U | 6/2012 |
| CN | 102992999 A | 3/2013 |
| CN | 103387492 * | 11/2013 |
| CN | 103387492 A | 11/2013 |
| CN | 103936581 A | 7/2014 |

OTHER PUBLICATIONS

Translation CN103387492 2017.*

* cited by examiner

*Primary Examiner* — Yevgeny Valenrod
*Assistant Examiner* — Blaine G Doletski
(74) *Attorney, Agent, or Firm* — Muncy, Geissler, Olds & Lowe, P.C.

(57) ABSTRACT

The present invention relates to a method for processing acetic acid solvent in an oxidizing unit of a PTA industrial apparatus; said method uses a pressure filter machine to filter crude terephthalic acid slurry, and then, using a multi-stage counter-current method, uses washing water to wash the acetic acid solvent, and, by means of setting up a bias-current and drainage, prevents residual liquid in the filtrate pipe from entering the next area following the rotation of the pressure filter machine, improving washing efficiency and reducing the amount of washing water; the present invention integrates the processes of filtering and washing crude terephthalic acid into a single pressure filter machine, such that the process is shorter, the occupied floor space is reduced, and energy consumption is lower. A method feeding nitrogen gas into the mother liquor tank and washing liquid tank is used to regulate the pressure balance of the system.

5 Claims, 8 Drawing Sheets

US 9,902,680 B2

METHOD FOR PROCESSING ACETIC ACID SOLVENT IN OXIDISING UNIT OF PTA INDUSTRIAL APPARATUS

FIELD OF THE INVENTION

The present invention relates to the technical field of energy conservation, in particular to a method for processing acetic acid solvent in crude terephthalic acid (CTA) in an oxidising unit of a PTA industrial apparatus.

DISCUSSION OF THE RELATED ART

The crude terephthalic acid slurry generated by the reactions in an oxidising unit of a PTA industrial apparatus contains a lot of acetic acid. According to the process requirements, the acetic acid has to be removed from the crude terephthalic acid before a refining process of PTA. Presently, the technology of "filtration by centrifuge or vacuum filter and drying by steam rotary dryer" is widely used in the industrial production. The process is mainly composed of a filtering area and a drying area.

As shown in FIG. 1, the process is performed as follows: conveying crude terephthalic acid slurry generated by the reactions and containing a lot of acetic acid to a centrifuge or a vacuum filter by a slurry pump at first, which in turn separates part of acetic acid from the slurry, and then conveying the resultant crude terephthalic acid filter cake to a steam rotary dryer to heat and dry it with steam indirectly, removing acetic acid from crude terephthalic acid by drying, using processing water to pulp the dried crude terephthalic acid and then conveying it to a refining unit.

The technology may have the following drawbacks.

1) The process flow is long and requires many accessory equipments

In such a technology, the filtering process and drying process are performed in different equipments, mainly including a vacuum filter, a steam rotary dryer, a washing tower, etc., as well as multiple accessory equipments and pipe fittings such as fans, pumps and valves. The process flow is long and thus involves complicated operations, which increase the equipment failure rate and potential safety hazards.

2) The equipments requires high investment cost and occupies a large floor space.

In such a technology, many equipments are involved, resulting in high investment for the equipments. Because of the high viscosity of crude terephthalic acid, a filter cartridge of a vacuum filter should be cleaned or replaced frequently. Therefore, the vacuum filters in the industrial apparatus generally operate with one of them being active and another one being standby, which further increases the investment of the pressure filters. Further, a relative large volume of the steam rotary dryer and a large number of auxiliary pressure filter machines increase the floor space.

3) High energy consumption

In such a technology, many active equipments that consume plenty of electrical energy are involved, including a centrifuge or vacuum filter machine, a steam rotary dryer, a pump, a fan, or the like. The steam rotary dryer evaporates acetic acid from crude terephthalic acid with latent heat of steam, which requires a large amount of steam and thus lots of heat energy. Further, a large amount of washing water is required for washing acetic acid from the dried tail gas. In addition, a large amount of processing water is required for pulping the dried crude terephthalic acid due to low moisture content thereof. Therefore, the technology has shortcomings of high energy consumption and high water consumption.

A kind of integrated equipment, namely pressure filter machine, has been used in the prior art to replace multiple sets of equipments including a vacuum centrifuge, a dryer, a washing tower, a powder tank or the like in the conventional process unit. For example, the Chinese Invention Patent Application Publication No. CN102476994A discloses a method for removing acetic acid from crude terephthalic acid by coarsely filtering crude terephthalic acid suspension by a pressure filter machine, and washing crude terephthalic acid with fresh water in several times sequentially to displace acetic acid in crude terephthalic acid.

However, as shown in FIG. 2, the washing liquid will be conveyed from a washing area to the next washing area via a filtrate pipe during the actual operation of the pressure filter, which will increase the concentration of the washing liquid in the next washing area and thus greatly reduce washing efficiency of the washing process. The consumption of washing water has to be increased so as to meet the requirements for product. Moreover, the pressure filter machine consists of multiple chambers. The content of acetic acid in a filter cake varies with the proceeding of the washing process, resulting in different pressure drops in each of the chambers. As a result, the seals between the chambers will be damaged in long-term operation and the washing liquid will be mixed among the chambers.

SUMMARY

The technical problem to be solved by the present invention is to provide a method for processing acetic acid (CTA) solvent in an oxidising unit of a PTA industrial apparatus to improve removal efficiency of acetic acid.

To solve the technical problem, the method for processing acetic acid solvent in an oxidising unit of a PTA industrial apparatus of the present invention comprises the following steps:

S100, conveying pressurized acetic acid CTA slurry from an oxidising unit of a upstream PTA industrial apparatus into a filtering area of a pressure filter to separate solid particles and acetic acid in the CTA slurry so as to form a CTA filter cake, separated mother liquor, and residual liquid in a filtrate pipe, discharging the separated mother liquor to a mother liquor tank, and biasing the residual liquid in the filtrate pipe to the mother liquor tank;

S200, washing the CTA filter cake stage by stage through a plurality of washing areas following the rotation of the pressure filter, wherein each washing area other than a washing area for the last-stage of washing is connected to a washing liquid tank respectively, each washing liquid tank providing washing liquid to its corresponding washing area to wash the CTA filter cake; wherein the washing area for the last-stage of washing uses fresh processing water as the washing liquid, while the remaining stages of washing supplies washing liquid from a later stage of washing back to a washing liquid tank of a former stage of washing in a multi-stage counter-current washing mode; and wherein a step of biasing residual liquid in the filtrate pipe of each stage of washing to the washing liquid tank of its corresponding stage is included during the stage-by-stage washing; and S300, conveying the CTA filter cake which has been processed by multiple washings to a unloading area following the rotation of the pressure filter, and then conveying the CTA filter cake of the unloading area to a pulping tank with the back blowing of nitrogen gas and the gravity so as to mix the CTA filter cake with external processing water and to pulp it, wherein a step of conducting residual liquid in the filtrate pipe to a filtrate tank and further conducting it to a washing liquid tank connected to a washing area for the penultimate stage of washing is included during the process of conveying the CTA filter cake to the unloading area.

For the method for processing acetic acid solvent in an oxidising unit of a PTA industrial apparatus, the first washing area is also connected to a corresponding recycling washing liquid tank, and the step S200 further comprises a step of recycling the washing liquid from the first stage of washing by the recycling washing liquid tank.

For the method for processing acetic acid solvent in an oxidising unit of a PTA industrial apparatus, the mother liquor tank and the washing liquid tanks are provided with a pressure regulating device respectively, wherein gas in a given tank is vented to a certain extent by the pressure regulating device on the tank when the pressure in the tank is higher than a preset pressure drop; while nitrogen gas is fed into a given tank by the pressure regulating device on the tank when the pressure in the tank is lower than the preset pressure drop.

The method for processing acetic acid solvent in an oxidising unit of a PTA industrial apparatus further comprises a step of feeding nitrogen gas to the mother liquor tank and the respective washing liquid tanks to maintain pressure balance of the whole system.

For the method for processing acetic acid solvent in an oxidising unit of a PTA industrial apparatus, in the step S100, the position of a separation block in a control head of the pressure filter machine is adjusted so as to discharge the mother liquor into the mother liquor tank and to bias residual liquid in the filtrate pipe into the mother liquor tank.

For the method for processing acetic acid solvent in an oxidising unit of a PTA industrial apparatus, in the step S200, the position of a separation block in a control head of the pressure filter machine is adjusted so as to bias residual liquid in the filtrate pipe of respective stage of washing to a washing liquid tank of a corresponding stage.

For the method for processing acetic acid solvent in an oxidising unit of a PTA industrial apparatus, in the step S300, the position of a separation block in a control head of the pressure filter machine is adjusted so as to conduct residual liquid in the filtrate pipe to the filtrate tank.

For the method for processing acetic acid solvent in an oxidising unit of a PTA industrial apparatus, in the step S300, the washing liquid in the filtrate tank is conveyed to a washing liquid tank connected to a washing area of the penultimate stage of washing by a pump.

Compared with the prior art, the present invention has the following advantages: The present invention employs bias-current and conduction techniques to bring the residual liquid in the filtrate pipes back to the washing liquid tanks of corresponding washing areas, which prevents the washing liquid of the previous area from entering the washing area of the next area and affecting the next stage of washing. With the bias-current and conduction techniques, the actual washing process is substantially identical with the ideal washing process, which increases the washing efficiency. The residual washing liquid can be separated by the conduction technique and reused as the washing liquid of the previous stage of washing, thus being capable of reducing the consumption of washing liquid and reducing the cost.

Furthermore, the present invention feeds nitrogen gas to regulate the pressures in the pressure filter, the mother liquor tank and the washing liquid tanks, thereby regulating the pressure balance of the system. The pressure adjusting method is convenient and accurate, and avoids damage of the seals between the chambers, thus avoiding the mixing of the washing liquid among the chambers.

The present invention will be described in detail in combination with accompanied drawings and preferred embodiments, but the drawings and preferred embodiments do not limit the present invention.

MARKS IN THE DRAWINGS

Figure 1:
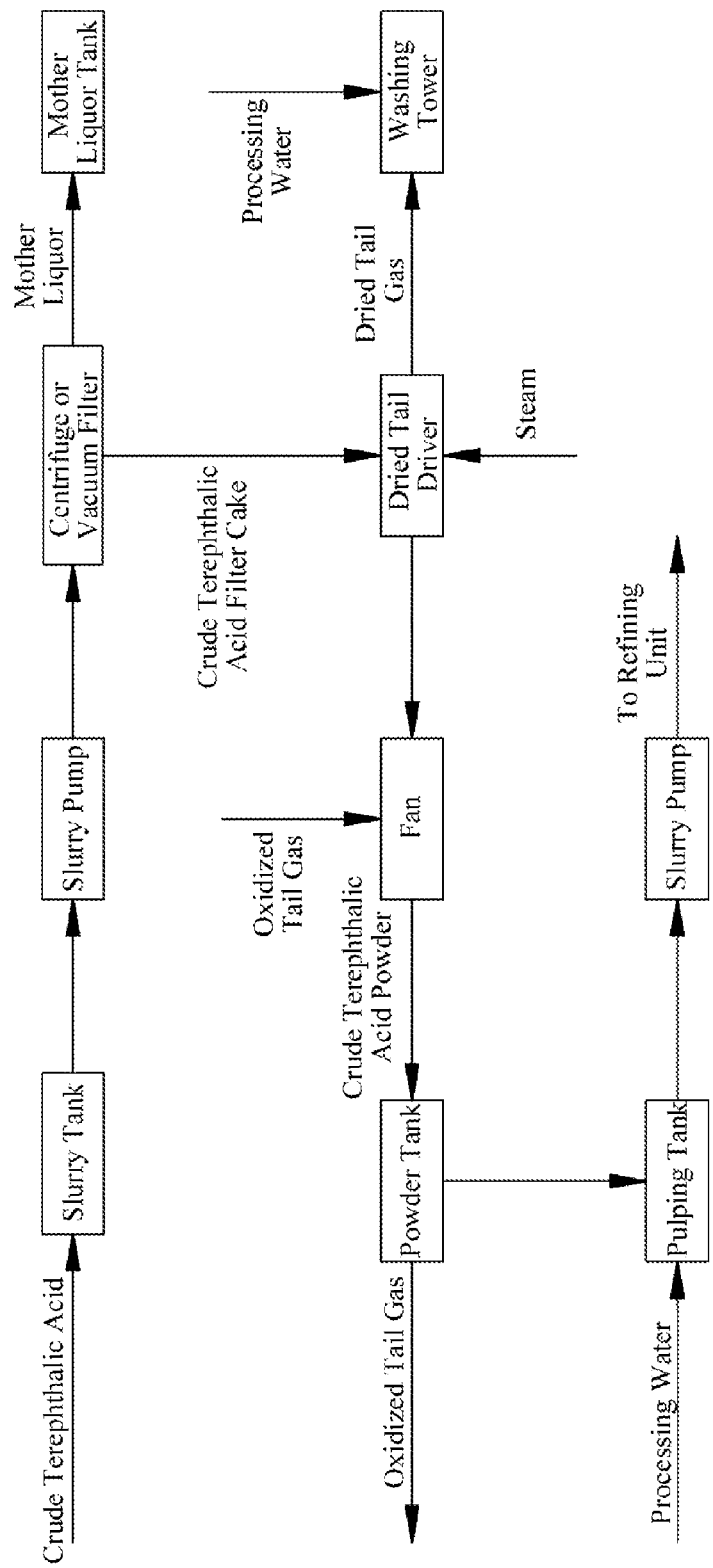
FIG. 1 is a flow block diagram of a centrifugal or vacuum filtration system for crude terephthalic acid in the prior art.
Figure 2:
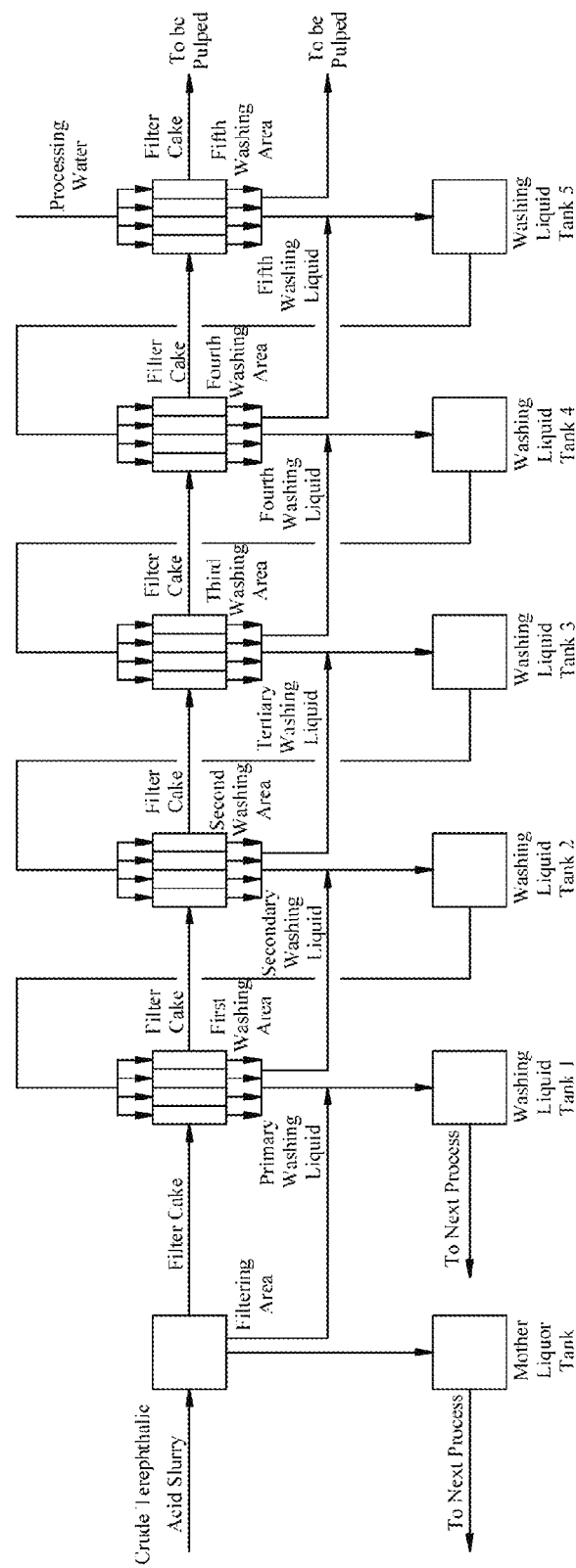
FIG. 2 is a schematic diagram of a multi-stage counter-current washing process for crude terephthalic acid without bias-current in the prior art.
Figure 3:
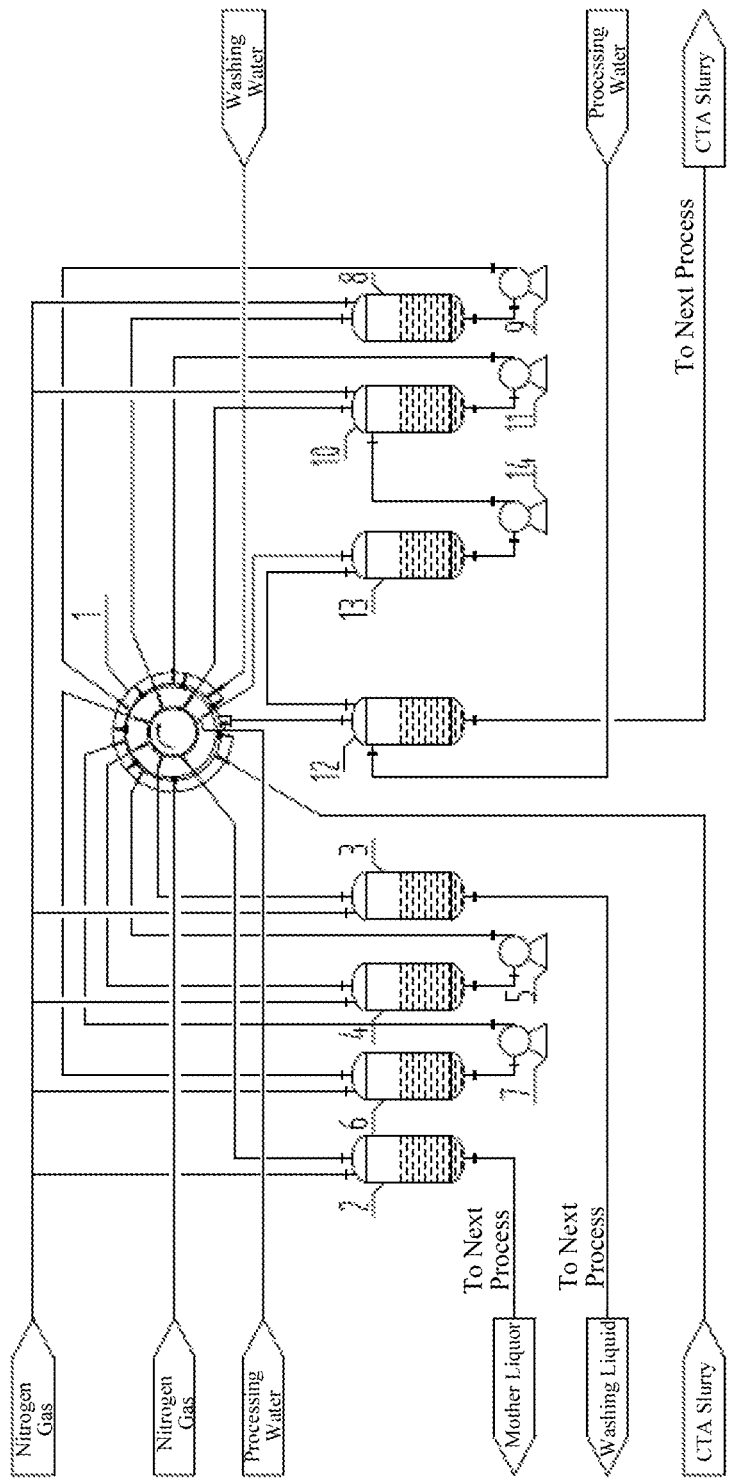
FIG. 3 is a process flow diagram of the present invention.
Figure 4:
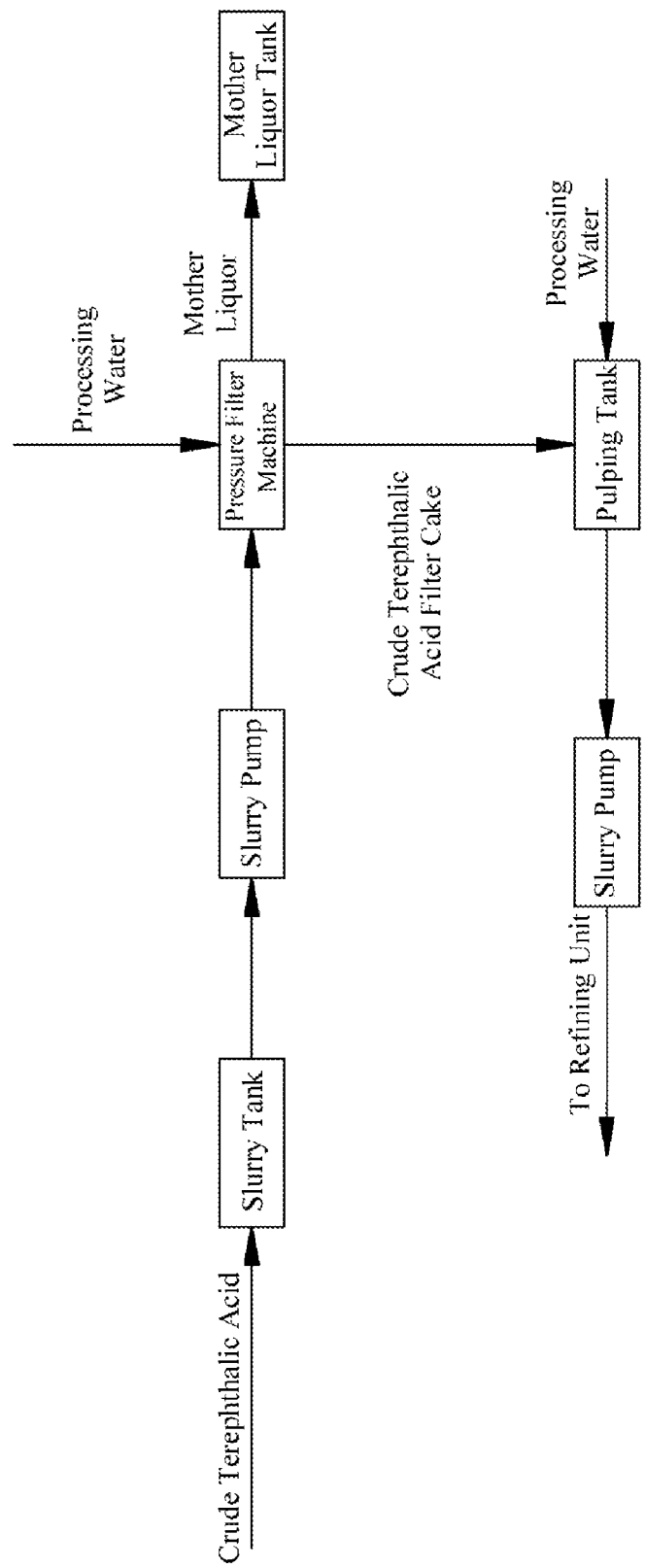
FIG. 4 is a process flow block diagram of the present invention.
Figure 5:
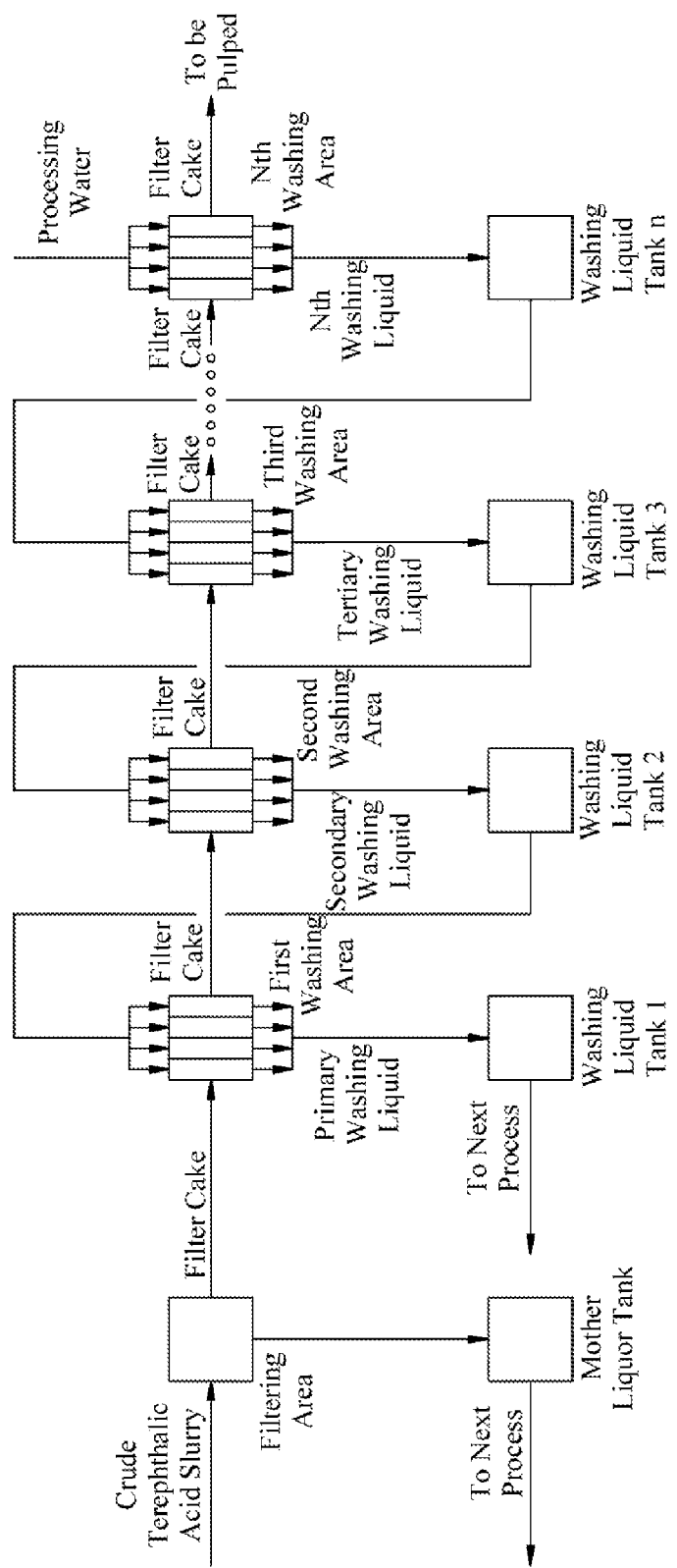
FIG. 5 is a schematic diagram of multi-stage counter-current washing process for crude terephthalic acid in the present invention.
Figure 6:
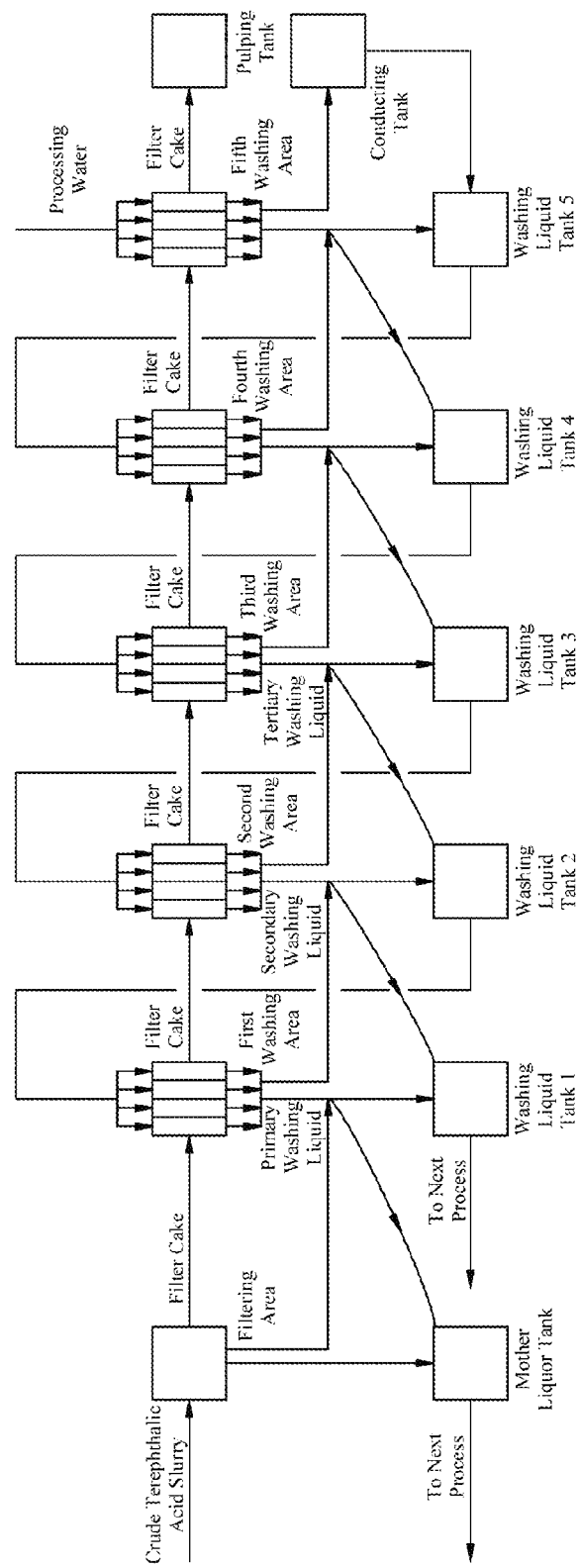
FIG. 6 is a schematic diagram of multi-stage counter-current washing of crude terephthalic acid with bias-current and conduction in the present invention.

1—Pressure filter machine
2—Mother liquor tank
3—Recycling washing liquid tank
4—Primary washing liquid tank
5—Primary washing liquid circulating pump
6—Secondary washing liquid tank
7—Secondary washing liquid circulating pump
8—Tertiary washing liquid tank
9—Tertiary washing liquid circulating pump
10—Fourth washing liquid tank
11—Fourth washing liquid circulating pump
12—Pulping tank
13—Filtrate tank
14—Conducting fluid circulating pump
18—Frame
19—Feeding area
20—Mother liquor chamber
21—Separation block A
22—Separation block a
23—Control head
24—Primary washing unit chamber
25—Separation block B
26—Primary filtrate chamber
27—Secondary washing unit chamber
28—Separation block b
29—Secondary filtrate chamber
30—Separation block C
31—Separation block c
32—Tertiary filtrate chamber
33—Tertiary washing unit chamber
34—Filtrate pipe
35—Separation block D
36—Separation block d
37—Fourth washing unit chamber
38—Fourth filtrate chamber
39—Separation block e 40—Separation block E
41—Fifth filtrate chamber
42—Fifth washing unit chamber
43—Separation block f
44—Separation block F
45—Unloading area I
46—Unloading area II
47—Separation block g
48—Separation block G
49—Regulation plate
50—Conduction port

DETAILED DESCRIPTION OF THE INVENTION

The present invention is described in detail in combination with accompanied drawings and preferred embodiments to further understand the object, solution and effects of the present invention, but the drawings and preferred embodiments do not limit the protection extent of appended claims of the present invention.

Refer to FIG. 3 to FIG. 6, a method for processing acetic acid (CTA) solvent in an oxidising unit of a PTA industrial apparatus in the embodiments of the present invention comprises the following steps:

a. Conveying crude terephthalic acid slurry generated in reactions and containing about 35% of TA solids and about 60% of acetic acid to a filtering area of a pressure filter machine 1 at a pressure of 0.3 MPG to 0.6 MPG, gradually separating the TA solid particles from the acetic acid in the slurry following the rotation of the pressure filter machine 1 to generate a CTA filter cake, and conveying the separated mother liquor to a mother liquor tank 2 via a control head of the pressure filter machine 1;

b. Conveying the filter cake generated by filtration to a first washing area following the rotation of the pressure filter machine 1, and at the same time, applying a pressure of 0.3 MPaG to 0.6 MPaG to the washing liquid in a primary washing liquid tank 4 and conveying the washing liquid to the first washing area by a primary washing liquid circulating pump 5 so as to continuously wash the filter cake (i.e. the first stage of washing), conveying the filter cake processed by the primary washing to a second washing area following the rotation of the pressure filter machine 1, and after the washing process, distributing the primary washing liquid via the control head and conveying it into a recycling washing liquid tank 3;

c. applying a pressure of 0.3 MPaG to 0.6 MPaG to the washing liquid in a secondary washing liquid tank 6 by a secondary washing liquid circulating pump 7, and conveying the washing liquid to the second washing area so as to continuously wash the filter cake processed by the primary washing (i.e. the second stage of washing), conveying the filter cake processed by the secondary washing to a third washing area following the rotation of the pressure filter machine 1, and after the washing process, distributing the secondary washing liquid via the control head and conveying it into a primary washing liquid tank 4;

d. applying a pressure of 0.3 MPaG to 0.6 MPaG to the washing liquid in a tertiary washing liquid tank 8 by a tertiary washing liquid circulating pump 9, and conveying the washing liquid to the third washing area so as to continuously wash the filter cake processed by the secondary washing (i.e. the third stage of washing), conveying the filter cake processed by the tertiary washing to a fourth washing area following the rotation of the pressure filter machine 1, and after the washing process, distributing the tertiary washing liquid via the control head and conveying it into the secondary washing liquid tank 6;

e. applying a pressure of 0.3 MPaG to 0.6 MPaG to the washing liquid in a fourth washing liquid tank 10 by a fourth washing liquid circulating pump 11, and conveying the washing liquid to the fourth washing area so as to continuously wash the filter cake processed by the tertiary washing (i.e. the fourth stage of washing), conveying the filter cake processed by the fourth washing to a fifth washing area following the rotation of the pressure filter machine 1, and after the washing process, distributing the fourth washing liquid via the control head and conveying it into the tertiary washing liquid tank 8; and f. conveying external process water of 90~100° C. to a fifth washing area of the pressure filter machine 1, to further wash the filter cake processed by the fourth washing (i.e. the fifth stage of washing) to remove the acetic acid from the crude terephthalic acid; after the washing process, distributing the fifth washing liquid via the control head and conveying it into the fourth washing liquid tank 10, conveying the filter cake processed by the fifth washing to a unloading area following the rotation of the pressure filter machine 1, conveying the filter cake to a pulping tank 12 with the nitrogen gas back blowing (0.1 to 0.3 MPaG) and gravity, so as to be mixed and pulped with the external process water.

In the steps, if a bias-current technique is not used, the residual liquid in the filtrate pipe would be carried into the next washing area following the rotation of the pressure filter machine 1 during the filtering and washing processes of crude terephthalic acid. The residual liquid would flow through the filtering area, the first washing area, the second washing area, the third washing area, the fourth washing area, the fifth washing area and the unloading area in sequence. To avoid such a case, the present invention provides a bias-current between different areas of the pressure filter machine 1. The bias current flows through the fifth washing area, the fourth washing area, the third washing area, the second washing area, the first washing area and the filtering area in sequence. With the bias-current, the residual liquid in the filtrate pipes can be brought back to the corresponding areas (see FIG. 6). Therefore, the method of the present invention also comprises a step of biasing the residual liquid in the filtrate pipe to the mother liquor tank; the above steps b, c, d and e comprise a step of biasing the residual liquid in the filtrate pipes of all stages of washing to the washing liquid tanks at corresponding stages; and the above step f also comprises a step of conducting the residual liquid in the filtrate pipe to a filtrate tank 13, and further conducting it to the washing liquid tank connected to the washing area for the penultimate stage of washing (i.e. the fourth washing liquid tank 10) during the process of conveying the CTA filter cake to the unloading area. Preferably, the washing liquid in the filtrate tank is conveyed to the fourth washing liquid tank 10 by a pump 14 (the pump is also referred as a conducting fluid circulating pump based on its function).

Because the pressure filter machine consists of multiple chambers, i.e., the filtering area and the first to fifth washing unit chambers, the content of the acetic acid in the filter cake varies during the washing processes, resulting in different pressure drops in each of the chambers. In such a case, the seals between the chambers will be damaged in long-term operation and the washing liquid will mixed among the chambers. To avoid it, the present invention feeds nitrogen gas to regulate the pressures in the pressure filter, the mother liquor tank and the respective washing liquid tanks, so as to regulate the pressure drops in the respective chambers and to make it substantially identical. Therefore, the method of the present invention also comprises a step of feeding nitrogen gas of 0.1 to 0.2 MPaG to the mother liquor tank and the respective washing liquid tanks so as to adjust the pressures in the mother liquor tank and the washing liquid tanks with nitrogen gas to maintain a pressure balance of the whole system. The mother liquor tank and the washing liquid tanks are provided with a pressure regulating device respectively, so that gas in a given tank may be vented to a certain extent by the corresponding pressure regulating device on the tank when the pressure in the tank is higher than a preset pressure drop; and a certain amount of nitrogen gas may be fed into a given tank by the pressure regulating device on the tank when the pressure in the tank is lower than the preset pressure drop, thereby maintaining the pressure balance of the whole system.

The present invention implements the bias-current and conduction by adjusting a position of a separation block in the control head of the pressure filter. That is, the residual liquid in the filtrate pipe is biased to the mother liquor tank by adjusting the position of the separation block in the control head of the pressure filter; the residual liquid in the filtrate pipes at respective stages of washing is biased to the washing liquid tank at corresponding stages by adjusting the position of the separation block in the control head of the pressure filter; and the residual liquid in the filtrate pipe is conducted to the filtrate tank by adjusting the position of the separation block in the control head of the pressure filter.

Figure 7:
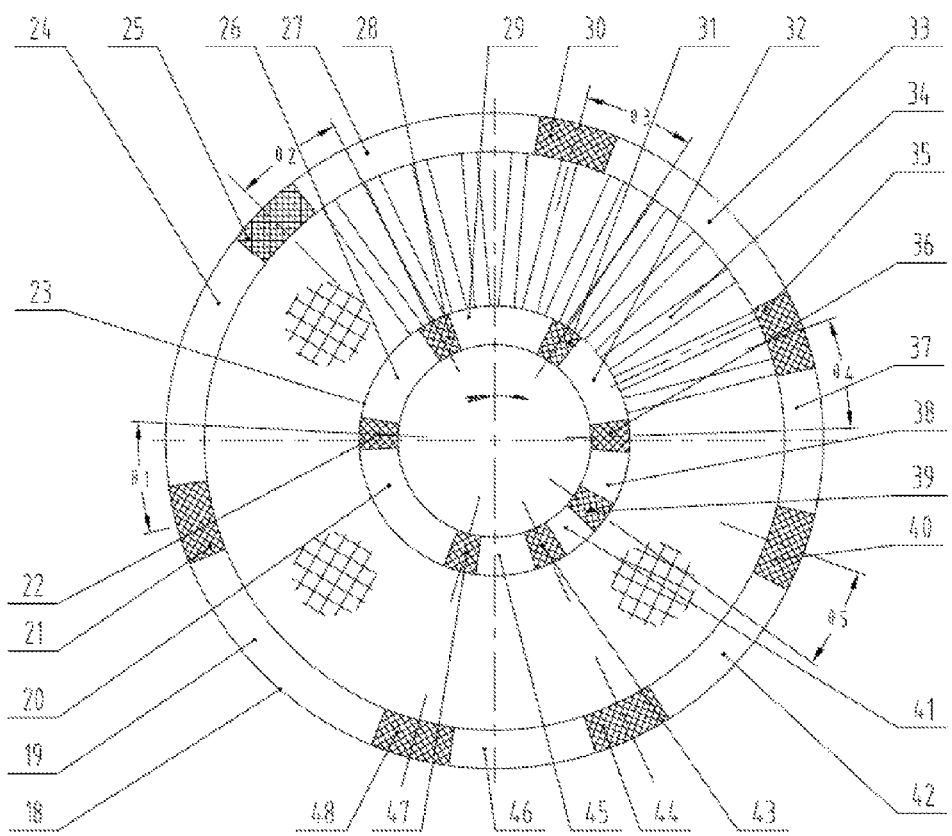
FIG. 7 is a simplified schematic diagram of a pressure filter machine as shown in FIG. 3.
Figure 8:
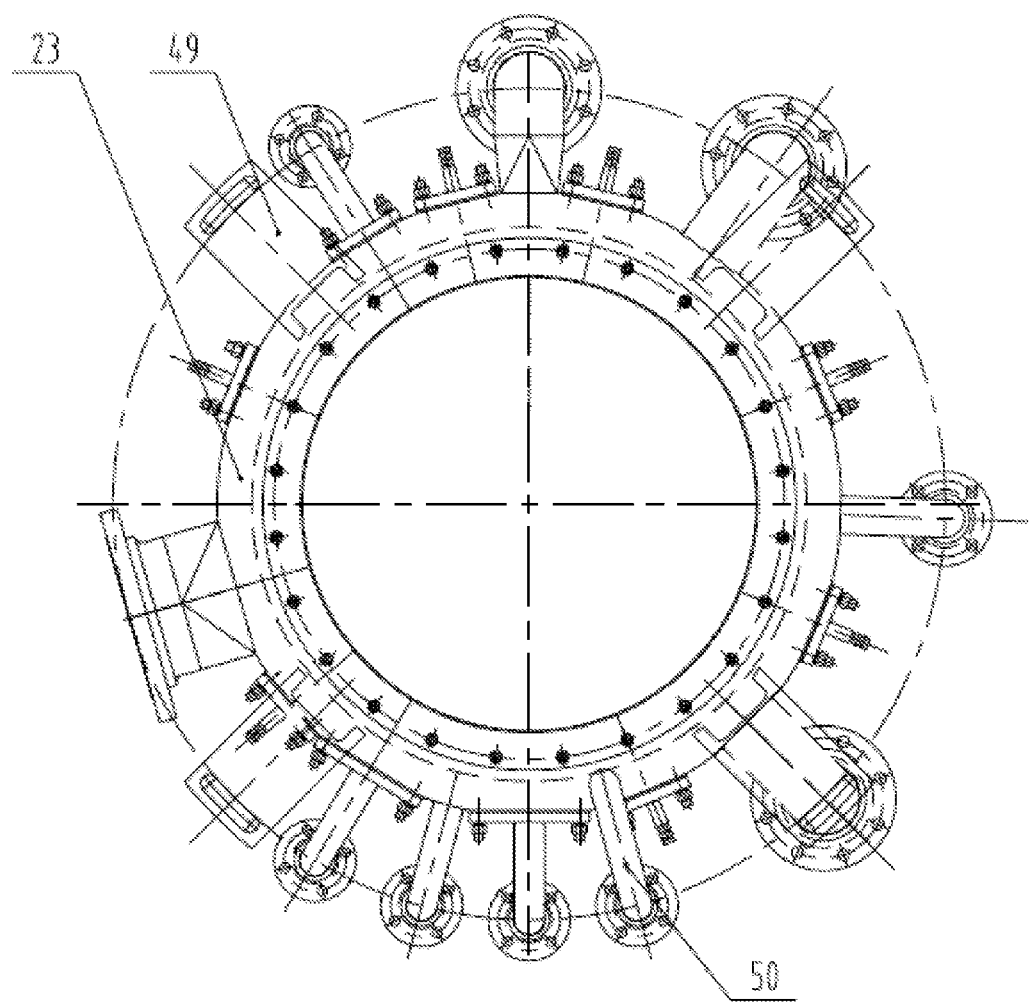
FIG. 8 is an outline drawing of a control head as shown in FIG. 7.

Refer to FIG. 7 and FIG. 8, the pressure filter machine 1 used in the present invention comprises a frame 18 and a control head 23. The frame 18 is divided into a feeding area 19, a primary washing unit chamber 24, a secondary washing unit chamber 27, a tertiary washing unit chamber 33, a fourth washing unit chamber 37, a fifth washing unit chamber 42 and an unloading area II 46 by a separation block A 21, a separation block B 25, a separation block C 30, a separation block D 35, a separation block E 40, a separation block F 44, and a separation block G 48. The control head 23 is divided into a mother liquor chamber 20, a primary filtrate chamber 26, a secondary filtrate chamber 29, a tertiary filtrate chamber 32, a fourth filtrate chamber 38, a fifth filtrate chamber 41 and an unloading area I 45 by a separation block a 22, a separation block b 28, a separation block c 31, a separation block d 36, a separation block e 39, a separation block f 43, and a separation block g 47. The separation block A 21, the separation block B 25, the separation block C 30, the separation block D 35, the separation block E 40, the separation block F 44, and the separation block G 48 correspond to the separation block a 22, the separation block b 28, the separation block c 31, the separation block d 36, the separation block e 39, the separation block f 43 and the separation block g 47 in a one-to-one manner. An adjusting plate 49 is arranged on the control head 23. A conduction port 50 is arranged at the end of the fifth filtrate chamber 41. The primary washing unit chamber 24, the secondary washing unit chamber 27, the tertiary washing unit chamber 33, the fourth washing unit chamber 37 and the fifth washing unit chamber 42 are respectively connected to the primary filtrate chamber 26, the secondary filtrate chamber 29, the tertiary filtrate chamber 32, the fourth filtrate chamber 38 and the fifth filtrate chamber 41 in a one-to-one manner, through a filtrate pipe 34.

To bias the residual liquid in the filtrate pipe to the mother liquor tank, the separation block a 22 of the control head 23 can be adjusted to allow the separation block a 22 to lead the separation block A 21 of the corresponding frame 18 by an angle $\theta 1$, so that the residual mother liquor may enter the corresponding mother liquor chamber 20 within the period in which a drum rotates by the angle $\theta 1$. The mother liquor chamber 20 is communicated with the mother liquor tank 2 through a pipe.

To bias the residual liquid in the filtrate pipe which has been processed by the first stage of washing to the primary washing liquid tank 4, the position of the separation block b28 between the primary filtrate chamber 26 and the secondary filtrate chamber 29 can be adjusted to allow the separation block b 28 to lead the separation block B 25 of the corresponding frame 18 by an angle $\theta 2$, so that the residual primary filtrate may enter the corresponding primary filtrate chamber 26 within the period in which the drum rotates by the angle $\theta 2$. The primary filtrate chamber 26 is communicated with the primary washing liquid tank 4 through a pipe.

To bias the residual liquid in the filtrate pipe which has been processed by the second stage of washing to the secondary washing liquid tank 6, the position of the separation block c31 between the secondary filtrate chamber 29 and the tertiary filtrate chamber 32 can be adjusted to allow the separation block c 31 to lead the separation block C 30 of the corresponding frame 18 by an angle $\theta 3$, so that the residual secondary filtrate may enter the corresponding secondary filtrate chamber 29 within the period in which the drum rotates by the angle $\theta 3$. The secondary filtrate chamber 29 is communicated with the secondary washing liquid tank 6 through a pipe.

To bias the residual liquid in the filtrate pipe which has been processed by the third stage of washing to the tertiary washing liquid tank 8, the position of the separation block d 36 between the tertiary filtrate chamber 32 and the fourth filtrate chamber 38 can be adjusted to allow the separation block d 36 to lead the separation block D 35 of the corresponding frame 18 by an angle $\theta 4$, so that the residual tertiary filtrate may enter the corresponding tertiary filtrate chamber 32 within the period in which the drum rotates by the angle $\theta 4$. The tertiary filtrate chamber 32 is communicated with the tertiary washing liquid tank 8 through a pipe.

To bias the residual liquid in the filtrate pipe which has been processed by the fourth stage of washing to the fourth washing liquid tank 10, the position of the separation block e 39 between the fourth filtrate chamber 38 and the fifth filtrate chamber 41 can be adjusted to allow the separation block e 39 to lead the separation block E 40 of the corresponding frame 18 by an angle $\theta 5$, so that the residual fourth filtrate may enter the corresponding fourth filtrate chamber 38 within the period in which the drum rotates by the angle $\theta 5$. The fourth filtrate chamber 38 is communicated with the fourth washing liquid tank 10 through a pipe.

To conduct the residual liquid in the filtrate pipe which has been processed by the fifth stage of washing to the filtrate tank 13, the position of the separation block f 43 between the fifth filtrate chamber 41 and the unloading area I 45 can be adjusted to correspond the separation block f 43 to the corresponding separation block F 44 of the frame 18. The residual liquid is further conducted from the conduction port 50 of the filtrate pipe to the filtrate tank 13 by a pumping unit, and then conveyed to the fourth washing liquid tank 10 by a conducting fluid circulating pump 14 connected to the filtrate tank 13.

After five times of washing, the filter cake enters the unloading area II 46 in the frame 18 following the rotation of the drum, and unloading gas enters from the unloading area I 45 of the control head 23 to back flush the filter cake, so as to unload the filter cake to the pulping tank 12 at which the filter cake is pulped to obtain a slurry, and to discharge the slurry.

Of course, the present invention may have other multiple embodiments. Those skilled in the art can make various corresponding changes and modifications according to the present invention without departing from the spirit and essence of the present invention, but these changes and modifications should be incorporated in the protection scope of the claims appended to the present invention.

INDUSTRIAL APPLICABILITY

The present invention employs bias-current and conduction techniques to bring the residual liquid in the filtrate pipes back to the washing liquid tanks of corresponding washing areas, which prevents the washing liquid of the previous area from entering the washing area of the next area and affecting the next stage of washing, and increases the washing efficiency. The residual washing liquid can be separated by the conduction technique and reused as the washing liquid of the previous stage of washing, thus being capable of reducing the consumption of washing liquid and the cost. Furthermore, the present invention feeds nitrogen gas to regulate the pressures in the pressure filter, the mother liquor tank and the washing liquid tanks, thereby regulating the pressure balance of the system. The pressure adjusting method is convenient and accurate, and avoids damage of the seals between the chambers, thus avoiding the mixing of the washing liquid among the chambers.

What is claimed is:

1. A method for processing acetic acid solvent in an oxidising unit of a purified teraphtalic (PTA) industrial apparatus, comprising the following steps:

S100, conveying pressurized crude teraphtalic acid (CTA) slurry containing acetic acid from an oxidising unit of a upstream PTA industrial apparatus into a filtering area of a pressure filter to separate solid particles and acetic acid in the CTA slurry so as to form a CTA filter cake, separated mother liquor, and mother liquor residual liquid in a filtrate pipe in the pressure filter, discharging the separated mother liquor to a mother liquor tank, and also biasing the mother liquor residual liquid in the filtrate pipe to the mother liquor tank, wherein the pressure filter includes a frame which is divided into a feeding area, a plurality of washing unit chambers, and a frame unloading area via a plurality of frame separation blocks, and a control head which is divided into a mother liquor chamber, a plurality of filtrate chambers, and a control head unloading area via a plurality of control head separation blocks, the plurality of frame separation blocks respectively corresponding to the control head separation blocks in a one-to-one manner, and the feeding area, the plurality of washing unit chambers, and the frame unloading area filtrate communicating with the mother liquor chamber, the plurality of filtrate chambers, and the control head unloading area in a one-to-one manner, wherein when a control head separation block between the mother liquor chamber and a filtrate chamber adjacent to the mother liquor chamber is set as a first control head separation block, and a frame separation block corresponding to the first control head separation block is set as a first frame separation block, the step of biasing the mother liquor residual liquid in the filtrate pipe to the mother liquor tank includes causing the mother liquor residual filtrate in the filtrate pipe to enter the mother liquor chamber by adjusting a position of the first control head separation block to allow it to lead the first frame separation block by a preset angle, so that the mother liquor residual filtrate enters the mother liquor tank communicated with the mother liquor chamber;

S200, washing the CTA filter cake in multiple stages through a plurality of washing areas following a rotation of the pressure filter, wherein, with respect to each washing area other than the last washing area among the plurality of washing areas, said washing area has a washing liquid tank connected thereto, and washing liquid which flows from a washing area next to said washing area after washing the CTA filter cake flows reversely to the washing liquid tank connected to said washing area as washing liquid, and with respect to the last washing area, fresh processing water is supplied to the last washing area as washing liquid, wherein, after washing in each washing area, residual liquid in the filtrate pipe corresponding to each washing area is biased to the washing liquid tank connected to the washing area, wherein, when a filtrate chamber corresponding to a current washing unit chamber for a current washing area is set as a current filtrate chamber, and a filtrate chamber corresponding to a next washing unit chamber for a next washing area is set as a next filtrate chamber, a control head separation block between the current filtrate chamber and the next filtrate chamber is set as a current control head separation block, and a frame separation block corresponding the current control head separation block is set as a current frame separation block, the step of biasing residual liquid in the filtrate pipe corresponding to each washing area to the washing liquid tank connected to the washing area includes causing the residual filtrate in the filtrate pipe to enter the current filtrate chamber by adjusting a position of the current control head separation block to allow it to lead the current frame separation block by a preset angle, so that the residual filtrate is biased to a washing liquid tank communicated with the current filtrate chamber; and S300, conveying the CTA filter cake which has been washed in multiple stages to an unloading area following the rotation of the pressure filter, and then conveying the CTA filter cake in the unloading area to a pulping tank to be mixed with external processing water and pulped, wherein a conduction port is arranged at an end of a last filtrate chamber corresponding to a washing unit chamber of the last washing area, the conduction port being connection to a filtrate tank, and wherein when a control head separation block between the last filtrate chamber and the control block unloading area is set as a last control head separation block, the last control head separation block is caused to correspond to a frame separation block corresponding to the last control head separation block by adjusting a position of the last control head separation block while the CTA filter cake enters the unloading area, so that the residual liquid in a filtrate pipe communicated with the conduction port is conducted to the filtrate tank and then conducted to a washing liquid tank connected to a penultimate washing area.

2. The method for processing acetic acid solvent in an oxidising unit of a PTA industrial apparatus of claim 1, wherein the first washing area further comprises a recycling washing liquid tank, and the step S200 further comprises a step of recycling the washing liquid from the first washing area after washing the CTA filter cake by using the recycling washing liquid tank.

3. The method for processing acetic acid solvent in an oxidising unit of a PTA industrial apparatus of claim 1, further comprising a step of feeding nitrogen gas to the mother liquor tank and the respective washing liquid tanks, wherein the pressure in the pressure filter, the mother liquor tank, and the washing liquid tanks are regulated to make the pressure drops in respective chambers of the pressure filter, the mother liquor tank, and the washing liquid tanks substantially identical.

4. The method for processing acetic acid solvent in an oxidising unit of a PTA industrial apparatus of claim 3, wherein the mother liquor tank and the washing liquid tanks are provided with a pressure regulating device respectively, wherein gas in one of the mother liquor tank and the washing liquid tanks is vented to a certain extent by the pressure regulating device on the tank when the pressure in the tank is higher than a preset pressure drop; while nitrogen gas is fed into a given tank by the pressure regulating device on the tank when the pressure in the tank is lower than the preset pressure drop.

5. The method for processing acetic acid solvent in an oxidising unit of a PTA industrial apparatus of claim 1, wherein in the step S300, the washing liquid in the filtrate tank is conveyed to a washing liquid tank connected to the penultimate washing area by a pump.

* * * * *